US006022538A

United States Patent [19]
Santoli et al.

[11] Patent Number: 6,022,538
[45] Date of Patent: *Feb. 8, 2000

[54] METHOD OF TREATING MALIGNANCIES

[75] Inventors: Daniela Santoli; Giovanni Rovera, both of Bryn Mawr; Alessandra Cesano, Philadelphia, all of Pa.

[73] Assignee: The Wistar Institute of Anatomy and Biology, Philadelphia, Pa.

[*] Notice: This patent is subject to a terminal disclaimer.

[21] Appl. No.: 08/847,000

[22] Filed: May 1, 1997

Related U.S. Application Data

[63] Continuation-in-part of application No. 08/472,686, Jun. 6, 1995, Pat. No. 5,702,702.

[51] Int. Cl.$^7$ .............................. C12N 5/08; A01N 63/00

[52] U.S. Cl. .................... 424/93.71; 424/93.7; 424/93.1; 435/325; 435/363; 435/366; 435/372.3

[58] Field of Search ............................... 424/93.7, 93.71, 424/93.1; 435/325, 363, 366, 372, 372.3, 78; 536/6.4; 514/492

[56] References Cited

U.S. PATENT DOCUMENTS 5,166,059  11/1992  Paston et al. ........................... 435/69.7
5,272,082  12/1993  Santoli et al. ......................... 435/372.3

OTHER PUBLICATIONS

S. Chan et al, "Mechanisms of Interferon–γInduction by Natural Killer Cell Stimulatory Factor (NKSF): Role of Transcription and mRNA Stability in the Synergistic Interactions Between NKSF and Interleukin–2 or Phorbal Diesters", *J. Immunol.*, 148(1) :92–98 (Jan. 1, 1992).

D. Santoli et al, "Synergistic and Antagonistic Effects of IL–1α and IL–4, Respectively, on the IL–2–Dependent Growth of a T Cell Receptor–γδ+Human T Leukemia Cell Line", *J. Immunol.*, 144(12) :4703–4711 (Jun. 15, 1990).

R. O'Connor et al, "Growth Factor–Dependent Differentiation Along the Myeloid and Lymphoid Lineages in an Immature Acute T Lymphocytic Leukemia", *J. Immunol.*, 145(11) :3779–3787 (Dec. 1, 1990).

R. O'Connor et al, "Growth Factor Requirements of Childhood Acute T–Lymphoblastic Leukemia: Correlation Between Presence of Chromosomal Abnormalities and Ability to Grow Permanently in Vitro", *Blood*, 77(7) :1534–1545 (Apr. 1, 1991).

A. Cesano et al, "Homing and Progression Patterns of Childhood Acute Lymphoblastic Leukemias in Severe Combined Immunodeficiency Mice", *Blood*, 77(11) :2463–2474 (Jun. 1, 1991).

A. Cesano et al, "Establishment of a Karyotypically Normal Cytotoxic Leukemic T–Cell Line from a T–All Sample Engrafted in SCID Mice", *Blood*, 81(10) :2714–2722 (May 15, 1993).

A. Cesano et al, "Effect of Human Interleukin 3 on the Susceptibility of Fresh Leukemia Cells to Interleukin–2–Induced Lymphokine Activated Killing Activity", *Leukemia*, 6(6) :567–573 (Jun., 1992).

A. Cesano et al, "Cytokine Modulation of the Susceptibility of Acute T–Lymphoblastic Leukemia Cell Lines to LAK Activity", *Leukemia*, 7(3):404–409 (Mar., 1993).

A. Cesano et al, "Mechanisms of MHC–Non–Restricted Lysis in Two Human Killer T Cell Lines", *Nat. Immun.*, 11(5):288–289 (Oct., 1992).

A. Cesano et al, "Two Unique Human Leukemic T–Cell Lines Endowed with a Stable Cytotoxic Function and a Different Spectrum of Target Reactivity Analysis and Modulation of Their Lytic Mechanisms", *In Vitro Cell Dev. Biol.*, 28A:648–656 (Sep.–Oct., 1992).

A. Cesano et al, "Inducible Expression of Granulocyte–Macrophage Colony–Stimulating Factor, Tumor Necrosis Factor–α, and Interferon–γ in Two Human Cytotoxic Leukemic T–Cell Lines", *In Vitro Cell Dev. Biol.*, 28A:657–662 (Sep.–Oct., 1992).

A. Cesano et al, "The Severe Combined Immunodeficient (SCID) Mouse as a Model for Human Myeloid Leukemias", *Oncogene*, 7:827–836 (May, 1992).

A. Cesano et al, "Treatment of Experimental Glioblastoma with a Human Major Histocompatibility Complex Nonrestricted Cytotoxic T Cell Line", *Cancer Research*, 55:96–101 (Jan. 1, 1995).

A. Cesano et al, "An Effective and Safe Marrow Purging Strategy Using a Lethally Irradiated Killer T Cell Clone", in *Advances in Bone Marrow Purging and Processing*, Fourth International Symposium, pp. 165–173 (Oct., 1994).

A. Cesano et al, "Cellular and Molecular Mechanisms of Activation of MHC Nonrestricted Cytotoxic Cells by IL–12", *J. Immunology*, 151:2943–2957 (Sep., 1993).

P. Greenberg et al, "Effector Mechanisms Operative in Adoptive Therapy of Tumor–Bearing Animals: Implications for the Use of Interleukin–2", *J. Biol. Resp. Modifiers*, 3(5) :455–461 (1984).

J. Klarnet et al, "Helper–Independent CD8+ Cytotoxic T Lymphocytes Express IL–1 Receptors and Require IL–1 for Secretion of IL–2", *J. Immunol.*, 142(7) :2187–2191 (Apr. 1, 1989).

M. Cheever et al, "Potential Uses of Interleukin 2 in Cancer Therapy", *Immunobiol.*, 172:365–382 (1986).

"First AIDS Gene–Transfer Clinical Comes Before RAC", *Biotechnology Newswatch*, 11(22) :1–3 (Nov. 18, 1991).

"RAC Phases Out Human Gene Therapy Unit; Approves Six New Protocols" *Biotechnology Newswatch*, 12(4) :9–10 (Feb. 17, 1992).

D. Ojcius et al, "Cell–Mediated Killing: Effector Mechanisms and Mediators", *Cancer Cells*, 2(5) :138–145 (May, 1990).

(List continued on next page.)

*Primary Examiner*—Ronald B. Schwadron
*Attorney, Agent, or Firm*—Howson and Howson

[57] ABSTRACT

A method of treating tumors which involves a synergistic combination of chemotherapy and cell therapy is provided. The method of the invention permits reduced amounts of chemotherapeutic agents to be administered, resulting in a reduction of the side effects often associated therewith.

9 Claims, 4 Drawing Sheets

E. Grimm et al, "Lymphokine–Activated Killer Cell Phenomenon: Lysis of Natural Killer–Resistant Fresh Solid Tumor Cells by Interleukin 2–Activated Autologous Human Peripheral Blood Lymphocytes", *J. Exp. Med.*, 155:1823–1841 (Jun., 1982).

S. Rosenberg, "Lymphokine–Activated Killer Cells: A New Approach to Immunotherapy of Cancer", *J. Natl. Can. Inst.*, 75(4) :595–603 (Oct., 1985).

S. Rosenberg et al, "Special Report—Observations on the Systemic Administration of Autologous Lymphokine–Activated Killer Cells and Recombinant Interleukin–2 to Patients with Metastatic Cancer", *New Engl. J. Med.*, 313(23) :1485–1492 (Dec. 5, 1985).

S. Rosenberg et al, "A Progress Report on the Treatment of 157 Patients with Advanced Cancer Using Lymphokine–Activated Killer Cells and Interleukin–2 or High–Dose Interleukin–2 Alone", *New Engl. J. Med.*, 316(15) :889–897 (Apr. 9, 1987).

S. Rosenberg, "What's New in General Surgery: The Development of New Immunotherapies for the Treatment of Cancer Using Interleukin–2", *Ann. Surg.*, 208(2) :121–135 (Aug., 1988).

S. Rosenberg et al, "Experience with the Use of High–Dose Interleukin–2 in the Treatment of 652 Cancer Patients", *Ann. Surg.*, 210(4) :474–485 (Oct., 1989).

M. Rosenstein et al, "Lymphokine–Activated Killer Cells: Lysis of Fresh Syngeneic Natural Killer–Resistant Murine Tumor Cells by Lymphocytes Cultured in Interleukin 2", *Cancer Res.*, 44:1946–1953 (May, 1984).

J. Mule et al, "Adoptive Immunotherapy of Established Pulmonary Metastases with LAK Cells and Recombinant Interleukin–2", *Science*, 225:1487–1489 (Sep. 28, 1984).

R. Lafreniere et al, "Successful Immunotherapy of Murine Experimental Hepatic Metastases with Lymphokine–Activated Killer Cells and Recombinant Interleukin 2", *Cancer Res.*, 45:3735–3741 t, 1985).

A. Mazumder et al, "Successful Immunotherapy of Natural Killer–Resistant Established Pulmonary Melanoma Metastases by the Intravenous Adoptive Transfer of Syngeneic Lymphocytes Activated in vitro by Interleukin 2", *J. Exp. Med.*, 159:495–507 (Feb., 1984).

W. West et al, "Constant–Infusion Recombinant Interleukin–2 in Adoptive Immunotherapy of Advanced Cancer", *New Engl. J. Med.*, 316(15) :898–905 (Apr. 9, 1987).

S. Topalian et al, "Expansion of Human Tumor Infiltrating Lymphocytes for use in Immunotherapy Trials", *J. Immunol. Meth.*, 102:127–141 (1987).

K. Itoh et al, "Interleukin 2 Activation of Cytotoxic T–Lymphocytes Infiltrating into Human Metastatic Melanomas", *Cancer Res.*, 46:3011–3017 (Jun., 1986).

R. Lee et al, "Cardiorespiratory Effects of Immunotherapy with Interleukin–2", *J. Clin. Oncol.*, 7(1) :7–20 (Jan., 1989).

M. Lotze et al, "Mechanisms of Immunologic Antitumor Therapy: Lessons from the Laboratory and Clinical Applications", *Hum. Immunol.*, 28:198–207 (1990).

J. Gootenberg et al, "A Biochemical Variant of Human T Cell Growth Factor Produced by a Cutaneous T Cell Lymphoma Cell Line", *J. Immunol.*, 129(4) :1499–1505 (Oct., 1982).

S. Arya et al, "T–Cell Growth Factor Gene: Lack of Expression in Human T–Cell Leukemia–Lymphoma Virus–Infected Cells", *Science*, 223:1086–1087 (Mar., 1984).

Y. Kaufmann et al, "Interleukin 2 Induces Human Acute Lymphocytic Leukemia Cells to Manifest Lymphokine–Activated–Killer (LAK) Cytotoxicity", *J. Immunol.*, 139(3) :977–982 (Aug. 1, 1987).

A. Kasid et al, "Human Gene Transfer: Characterization of Human Tumor–Infiltrating Lymphocytes as Vehicles for Retroviral–Mediated Gene Transfer in Man", *Proc. Natl. Acad. Sci. USA*, 87:473–477 (Jan., 1990).

K. Nishihara et al, "Augmentation of Tumor Targeting in a Line of Glioma–Specific Mouse Cytotoxic T–Lymphocytes by Retroviral Expression of Mouse –Interferon Complementary DNA", *Cancer Research*, 48:4730–4735 (Sep. 1, 1988).

H. Karasuyama et al, "Autocrine Growth and Tumorigenicity of Interleukin 2–Dependent Helper T Cells Transfected with IL–2 Gene", *J. Exp. Med.*, 169:13–25 (Jan., 1989).

T. Torigoe et al, "Interleukin 4 Inhibits IL–2–Induced Proliferation of a Human T–Leukemia Cell Line without Interfering with p56–LCK Kinase Activation", *Cytokine*, 4(5) :369–376 (Sep., 1992).

T. Torigoe et al, "Interleukin–3 Regulates the Activity of the LYN Protein–Tyrosine Kinase in Myeloid–Committed Leukemic Cell Lines", *Blood*, 80(3) :617–624 (Aug. 1, 1992).

B. Perussia et al, "Natural Killer (NK) Cell Stimulatory Factor or IL–12 has Differential Effects on the Proliferation of TCR–$\alpha\beta^+$, TCR–$\gamma\delta^+$ T Lymphocytes, and NK Cells", *J. Immunol.*, 149(11) :3495–3502 (Dec. 1, 1992).

B. Lange et al, "Pediatric Leukemia/Lymphoma with t(8;14) (q24;q11)", *Leukemia*, 6(7) :613–618 (Jul., 1992).

T. Han et al, "Stimulating Capacity of Blast Cells from Patients with Chronic Myelocytic Leukaemia, in Blastic Crisis in "One–Way" Mixed Lymphocyte Reaction: Lack of Evidence for T Lymphoblastic Conversion", *Immunology*, 35:299–305 (1978).

B. Rouse et al, "Consequences of Exposure to Ionizing Radiation for Effector T Cell Function In Vivo", *Viral Immunology*, 2(2) :69–78 (1989).

A. Stern et al, "Purification to Homogeneity and Partial Characterization of Cytotoxic Lymphocyte Maturation Factor from Human B–Lymphoblastoid Cells", *Proc. Natl. Acad. Sci. USA*, 87:6808–6812 (Sep., 1990).

K. Foon, "Biological Response Modifiers: The New Immunotherapy", *Cancer Research*, 49, 1621–1639 (Apr., 1989).

T. Boon, "Tumor Antigens Recognized by Cytolytic T Lymphocytes: Present Prespectives for Specific Immunotherapy" *Int. J. Cancer*, 54:177–180 (Jan., 1993).

M. Osband et al., "Problems in the Investigational Study and Clinical Use of Cancer Immunotherapy" *Immunology Today*, 11: 402–404 (1990).

A. Cesano et al, "Antitumor Efficacy of a Human Major Histocompatibility Complex Nonrestricted Cytotoxic T–Cell Line (TALL–104) in Immunocompetent Mice Bearing Syngeneic Leukemia", *Cancer Research*, 56:4444–4452 (Oct. 1, 1996).

A. Cesano et al, "Phase I Clinical Trial with a Human Major Histocompatibility Complex Nonrestricted Cytotoxic T–Cell Line (TALL–104) in dogs with Advanced Tumors", *Cancer Research*, 56:3021–3029 (Jul. 1, 1996).

A. Cesano et al, "Effects of Lethal Irradiation and Cyclosporin A Treatment on the Growth and Tumoricidal Activity of a T Cell Clone Potentially Useful in Cancer Therapy", *Cancer Immunol. Immunother.*, 40:139–151 (Mar., 1995).

A. Cesano et al, "Reversal of Acute Myelogenous Leukemia in Humanized SCID Mice Using a Novel Adoptive Transfer Approach", *J. Clin. Invest.*, 94:1076–1084 (Sep., 1994).

A. Cesano et al, "Synergistic Effects of Adriamycin and TALL–104 Cell Therapy Against a Human Gastric Carcinoma in Vivo", *Anticancer Research*, 17:1887–1892 (May–Jun., 1997).

A. Cesano et al, "Toxicological and Immunological Evaluation of the MHC–non–restricted Cytotoxic T Cell Line TALL–104", *Cancer Immunol. Immunother.*, 44:125–136 (May, 1997).

S. Visonneau et al, "Cell Therapy of a Highly Invasive Human Breast Carcinoma Implanted in Immunodeficient (SCID) Mice", *Clinical Cancer Research*, 3:1491–1500 (Sep., 1997).

S. Visonneau et al, "Successful Treatment of Canine Malignant Histiocytosis with the Human Major Histocompatibility Complex Nonrestricted Cytotoxic T–Cell Line TALL–104", *Clinical Cancer Research*, 3:1789–1797 (Oct., 1997).

METHOD OF TREATING MALIGNANCIES

CROSS-REFERENCE TO RELATED APPLICATION

This is a continuation-in-part of U.S. patent application Ser. No. 08/472,686, filed Jun. 6, 1995 which issued as U.S. Pat. No. 5,702,702.

FIELD OF THE INVENTION

The invention relates generally to the treatment of cancers, and more particularly, to the treatment of drug-resistant cancers.

BACKGROUND OF THE INVENTION

The use of adoptive transfer therapy in combination with chemotherapy to treat neoplastic disease forms the basis for adoptive chemo-immunotherapy. In murine models, adoptive transfer of T cells in conjunction with administration of some chemotherapeutic agents has successfully treated significant numbers of tumor-bearing hosts [P. Greenberg et al, *J. Exp. Med.,* 161:1122–1134 (1985); M. Bookman et al, *J. Immunol.,* 139:3166–3170 (1987); and F. Fornelle et al, *Int. J. Cancer,* 42:952–957 (1988)]. Results from the few clinical trials conducted so far have demonstrated that TIL/IL-2 therapy together with adriamycin, mitomycin or cyclophosphamide treatment represents a promising therapeutic approach in patients with metastatic or primary liver tumors and melanoma [A. Kawata et al, *Am. J. Clin. Oncol.,* 18:257–262 (1995); S. Rosenberg et al, *N. Engl. J. Med.,* 319:1676–1680 (1988); and J. Gold et al, *Eur. J. Cancer,* 31A:698–708 (1995)]. The mechanisms underlying the improved antitumor effects obtained with the combined regimens have not been fully elucidated. However, the immunomodulatory activity displayed by some chemotherapeutic agents seems to play a critical role in determining the superiority of chemo-immunotherapy versus single agent treatment [M. Awwad et al, *Immunology,* 65:87–92 (1988) and R. North, *J. Exp. Med.,* 155:1063–1074 (1982)]. Despite these clinical results, the toxicity involved with LAK or TIL/IL-2 therapy [K. Margolin et al, *J. Clin. Oncol.,* 7:486 (1989)] and the scarcity of tumor specimen for preparation and expansion of TIL [S. Topalian et al, *J. Immunol. Meth.,* 102:127–141 (1987)] are important limiting factors for the use of cell therapy in conjunction with other approaches.

A new adoptive transfer strategy to cancer that might overcome the limitations of LAK and TIL therapy because it does not require the concomitant administration of exogenous, toxic cytokines, such as IL-2, for efficacy have been developed. This approach is based on the use of a lethally irradiated human T cell line (TALL-104), (CD3/TCRαβ$^+$CD8$^+$CD16$^-$) [A. Cesano et al, *In Vitro Cell. Dev. Biol.,* 28A:648 (1992); A. Cesano et al, *J. Immunol.,* 151:2943–2957 (1993); and A. Cesano et al, *Cancer Immunol. Immunoth.,* 40:139 (1995)], which is endowed with MHC non-restricted killer activity against a broad range of tumors across several species, while sparing cells from normal tissues. Studies in immunodeficient and immunocompetent murine models with transplantable tumors and in canines with spontaneously arising cancers, suggest the potential of this cell line as an anti-tumor agent in a clinical setting [A. Cesano et al, *J. Clin. Invest.,* 94:1076 (1994); A. Cesano et al, *Cancer Res.,* 55:96 (1995); A. Cesano et al, *Cancer Res.,* 56:3021 (1996); and A. Cesano et al, *Cancer Res.,* 56:4444–4452 (1996)].

However, despite the progress made in recent years in the management of various forms of hematological and non-hematological malignancies (i.e., solid tumors), it has become clear that single therapeutic approaches, such as surgery, chemotherapy, radiation therapy, and biological therapies are often not effective in eradicating or drastically reducing tumor burden. Optimal therapy for refractory tumors requires multiple combination approaches.

What are needed are methods of treating cancers which are resistant to single forms of treatment, and particularly, which are resistant to chemotherapy. In addition, methods of reducing the toxicity of otherwise effective anti-cancer chemotherapeutic regimens are needed.

SUMMARY OF THE INVENTION

The invention provides methods of treating a tumor in a mammal and for reducing the toxicity of a chemotherapeutic agent to a mammal.

In one aspect, the invention provides a method of treating cancer in a mammal. The method involves co-administering to the mammal a course of therapy with a chemotherapeutic agent and a course of therapy with cells characterized by non-MHC restricted cytotoxic activity. Surprising, the inventors have found that this co-administration has a anti-tumor effect which exceeds the additive anti-tumor effects of chemotherapy and cell therapy alone.

In another aspect, the invention provides a method of treating a drug-resistant cancer, and particularly, a drug-resistant tumor in a mammal. The method involves co-administering to the mammal a course of therapy with a chemotherapeutic agent and a course of therapy with cells characterized by non-MHC restricted cytotoxic activity. Desirably, the cell line is administered during the course of treatment with the chemotherapeutic agent.

In still another aspect, the invention provides a method of reducing the toxicity of a chemotherapeutic agent to a mammal. The method involves co-administering to the mammal a course of therapy with a chemotherapeutic agent and a course of therapy with cells characterized by non-MHC restricted cytotoxic activity. Advantageously, the combined effect of the cell line and the chemotherapeutic agent permits a lower dose of chemotherapeutic agent to be effective than is required in the absence of the cell line.

Other aspects and advantages of the present invention are described further in the following detailed description of the preferred embodiments thereof.

DETAILED DESCRIPTION OF THE INVENTION

Figure 1A:
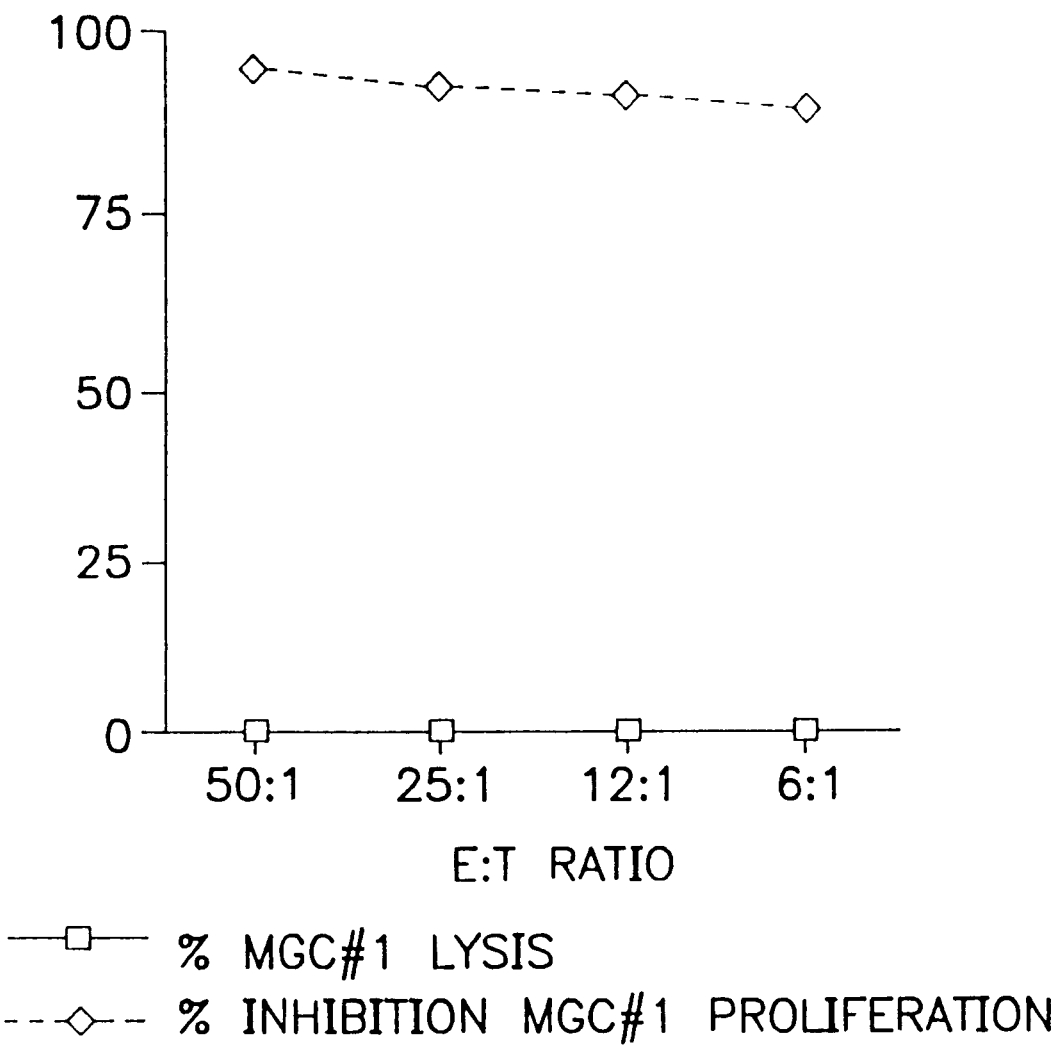
FIG. 1A illustrates the cytotoxic and cytostatic activities of γ-irradiated TALL-104 cells against MGC #1 tumor cells in 18-hour $^{51}$Cr-release and 18-hour $^3$HTdR uptake inhibition assays, respectively. SD values <2.0 are not shown.

The present invention provides methods and compositions for the treatment of solid tumors. Surprisingly, the inventors have found that, in certain embodiments, this co-administration of chemotherapy and cell therapy, as described in detail below, provides a synergistic effect, i.e., an anti-cancer effect which exceed the additive anti-cancer effects of the chemotherapy or cell therapy alone, or their additive effects. In other embodiments, this co-administration provides anti-cancer effects which exceed administration of the chemotherapy or cell therapy alone. Further, the method of the invention is useful in overcoming resistance of a cancer to single therapeutic agents through mechanisms independent from the host immune system. Yet another advantage of the present invention is that it permits a lower dose of chemotherapeutic agent to be used where desired, e.g., to reduce undesirable side effects associated therewith.

According to the invention, a course of chemotherapy with a chemotherapeutic agent is administered in conjunction with cell therapy to a human or veterinary patient. Each of these therapies is discussed in more detail below. The method of the invention provides for concurrent administration, sequential administration, or combined administration. These means of administration are termed herein, co-administration.

The methods of the invention may be combined with other therapies useful in the treatment of cancer. It is also anticipated that this treatment may be administered to a mammal which is already immunosuppressed due to disease. The evaluation of the immune status of the human or veterinary patient may be readily determined by one of skill in the art.

Chemotherapy

Chemotherapeutic agents are well known to those of skill in the art. Examples of such chemotherapeutics include alkylating agents, antibiotics, antimetabolitic agents, plant-derived agents, and hormones. Among the suitable alkylating agents are nitrogen mustards, such as cyclophosphamide, aziridines, alkyl alkone sulfonates, nitrosoureas, nonclassic alkylating agents, such as dacarbazine, and platinum compounds, such as carboplatin and cisplatin. Among the suitable antibiotic agents are dactinomycin, bleomycin, mitomycin C, plicamycin, and the anthracyclines, such as doxorubicin (also known as adriamycin) and mitoxantrone. Among the suitable antimetabolic agents are antifols, such as methotrexate, purine analogues, pyrimidine analogues, such as 5-fluorouracil (5-FU) and cytarabine, enzymes, such as the asparaginases, and synthetic agents, such as hydroxyurea. Among the suitable plant-derived agents are vinca alkaloids, such as vincristine and vinblastine, taxanes, epipodophyllotoxins, such as etoposide, and camptothecan. Among suitable hormones are steroids. Currently, the preferred drug is adriamycin. However, other suitable chemotherapeutic agents, including additional agents within the groups of agents identified above, may be readily determined by one of skill in the art depending upon the type of solid tumor being treated, the condition of the human or veterinary patient, and the like.

Suitable dosages for the selected chemotherapeutic agent are known to those of skill in the art. For example, where the agent is adriamycin, suitable dosage may include 30 mg/m$^2$, administered intravenously, twice at 1 week intervals. However, one of skill in the art can readily adjust the route of administration, the number of doses received, the timing of the doses, and the dosage amount, as needed. Further, because co-administration of chemotherapy with the cell line according to the method of the invention provides enhanced results, one of skill in the art may find it desirable to reduce the dose of chemotherapeutic agent administered to reduce any toxic side effects associated therewith.

Bearing in mind the above considerations, generally, a suitable dose for a given chemotherapeutic agent when administered according to the method of the invention, is between 0.01 µg/mL to about 1 mg/mL, and more preferably, between 0.01 µg/mL to about 1 µg/mL. Such a dose, which may be readily adjusted depending upon the particular drug or agent selected, may be administered by any suitable route, including, e.g., intravenously, intradermally, by direct site injection, intraperitoneally, intranasally, or the like. Doses may be repeated as needed.

Cell Therapy

According to the invention, cell therapy involves administration of cells to a human or veterinary patient. The cells useful in the method of the invention have non-MHC restricted killer activity against a broad range of tumors across several species, while sparing cells from normal tissues. Desirably, these cells are derived from a stable cell line.

Examples of suitable cell lines include, e.g., TALL-104, TALL-103/2, TALL-107, YT, and natural killer cell lines, such as NK-92. However, one of skill in the art could readily select other appropriate cell lines which are characterized by non-MHC restricted killer activity as described above. Such cell lines are available from the American Type Culture Collection (ATCC), 10801 University Boulevard, Manassas, Va. 20110-2209, as well as from a variety of academic and commercial sources. For example, the TALL-104 cell line is available from the ATCC under accession number CRL 11386. The TALL-103/2 and TALL-107 cell lines are being maintained in the laboratories at The Wistar Institute of Anatomy and Biology, Philadelphia, Pa. Sources of other cell lines useful in the invention can be readily determined by one of skill in the art.

Desirably, prior to use in the methods of the invention, cells obtained from one or more of the selected cell lines would be treated in a manner which irreversibly arrests cell proliferation, but does not interfere with the cytotoxic activity of the cells. Currently, a preferred treatment method involves irradiation, and particularly γ-irradiation. Although γ-irradiation is used as an example, it is anticipated that other methods could be used to stop the growth of the cells, such as treatment with chemical agents that affect DNA synthesis, such as mitomycin C. One of skill in the art can readily select appropriate methods for arresting growth.

Currently, the preferred cells are derived from a TALL-104 cell line, and the cells have been modified by lethal γ-irradiation as described below. TALL-104 cells may be modified in such a way as to provide them with an increased cytotoxicity against tumor and virus-infected targets. Such modification methods have been described in detail in WO 94/26284, published Nov. 24, 1994, which is incorporated by reference herein. For example, one modification step includes in vitro treatment of the TALL-104 cells with a selected cytokine or combination of cytokines. For example, the two interleukins, recombinant human (rh) interleukin (IL) IL-2 and rhIL-12, when used independently to treat the cell line, induce the cell line's cytotoxic activity. When these cytokines are used together to modify the cell line, the modified cell line displays additive or increased cytotoxic effects. This results in a significant increase in cytotoxic activity and recycling capability, ultimately leading to 100% elimination of tumor targets at an E:T ratio <0.1:1 [Cesano et al, *J. Immunol.*, 151:2943 (1993)].

Another modification step of this invention involves the exposure of the TALL-104 cell line to lethal irradiation to confer irreversible loss of growth capability with full retention of cytotoxic activity, both in vitro and in vivo. This is achieved by subjecting the cell lines to γ-irradiation just prior to their use. Preferably, the cells are irradiated at 4000 rads using a $^{137}$Cs source.

Irradiation of TALL-104 cells provides a modified cytotoxic cell line that has lost its proliferative ability and, therefore, the possibility of growing in an unrestrained fashion in the recipient organism. In fact, unlike their non-irradiated counterparts, modified γ-irradiated TALL-104 cells of this invention transplanted into SCID mice do not cause leukemia.

Preferably, modified TALL-104 cells are prepared as follows. TALL-104 cells (ATCC CRL 11386) are exponentially grown in tissue culture in the presence of recombinant human (rh) IL-2. If desired, IL-12 can be added for about 18 hrs to enhance the killing activity of the cell line. The cytokine-treated TALL-104 cells are then γ-irradiated, preferably at about 4,000 rads. The irradiation may be continued for a selected time, such as about 30 minutes. The resulting cell line is referred to as the modified TALL-104 cell line.

Desirably, about $10^4$ to about $10^{12}$, and preferably about $10^{12}$, of the cells selected for use in the invention are suspended in a pharmaceutically acceptable carrier and administered daily for the desired length of time by an appropriate route. One particularly desirable carriers is saline. However, other suitable carriers are well known to those of skill in the art and may be readily selected.

As discussed above, cell therapy may be concurrent with chemotherapy, start shortly after the end of the chemotherapeutic regimen, or be combined into a single therapeutic regimen. Alternatively, and currently less desirable, is administration of cell therapy preceding chemotherapy. Currently, the preferred embodiment involves administration of the cell therapy during the course of chemotherapy, and particularly, following saturation of the target tissue (i.e., the tumor) with the chemotherapeutic agent. Thus, the cell therapy is desirably administered one to about four days following administration of the chemotherapeutic agent. Administration of cell therapy is repeated as needed.

As one example, cells (e.g., about $2 \times 10^7$ γ-irradiated TALL-104 cells) may be administered daily for 2 weeks, concurrently with chemotherapy. Alternatively, the cells may be administered starting shortly after the end of chemotherapy. In yet another alternative, the cell therapy may be administered at different doses, different intervals (rather than daily) or for a shorter or longer period of time.

Cell therapy may be administered by injection, e.g., intravenously, or by any of the means discussed above in connection with chemotherapy. Neither the time nor the mode of administration is a limitation on the present invention. As with chemotherapy, cell therapy regimens may be readily adjusted taking into account such factors as the cytotoxicity of the selected cell line, the type of solid tumor being treated, the stage of the disease and the condition of the patient, among other considerations known to those of skill in the art.

In a currently preferred embodiment, the method of the invention involves co-administration of γ-irradiated TALL-104 cells and adriamycin. As illustrated in the examples below, although these treatments alone did not inhibit tumor growth, synergistic antitumor effects were seen following the condition of the veterinary or human patient.

Pharmaceutical Compositions

As an alternative to the separate administration of chemotherapy and cell therapy as described above, the compositions of the invention facilitate a combined chemotherapy-cell therapy approach.

In another aspect, the present invention provides pharmaceutical compositions which contain a desired chemotherapeutic agent or agents and a desired cell, as described herein. These compositions may further contain a pharmaceutically acceptable carrier. Suitable carriers include, e.g., saline, phosphate buffered saline, and saline with 5% HSA or PPF. Other suitable carriers are well known to those of skill in the art and are not a limitation on the present invention. Similarly, one of skill in the art may readily select other desired components for inclusion in a pharmaceutical composition of the invention, and such components are not a limitation of the present invention. A currently preferred composition of the invention contains adriamycin and modified TALL-104 cells, as defined herein.

The compositions of the invention may be administered by the routes and according to the regimens described above for chemotherapy and/or cell therapy. Alternatively, other suitable routes and regimens may be readily determined by one of skill in the art.

Figure 2:
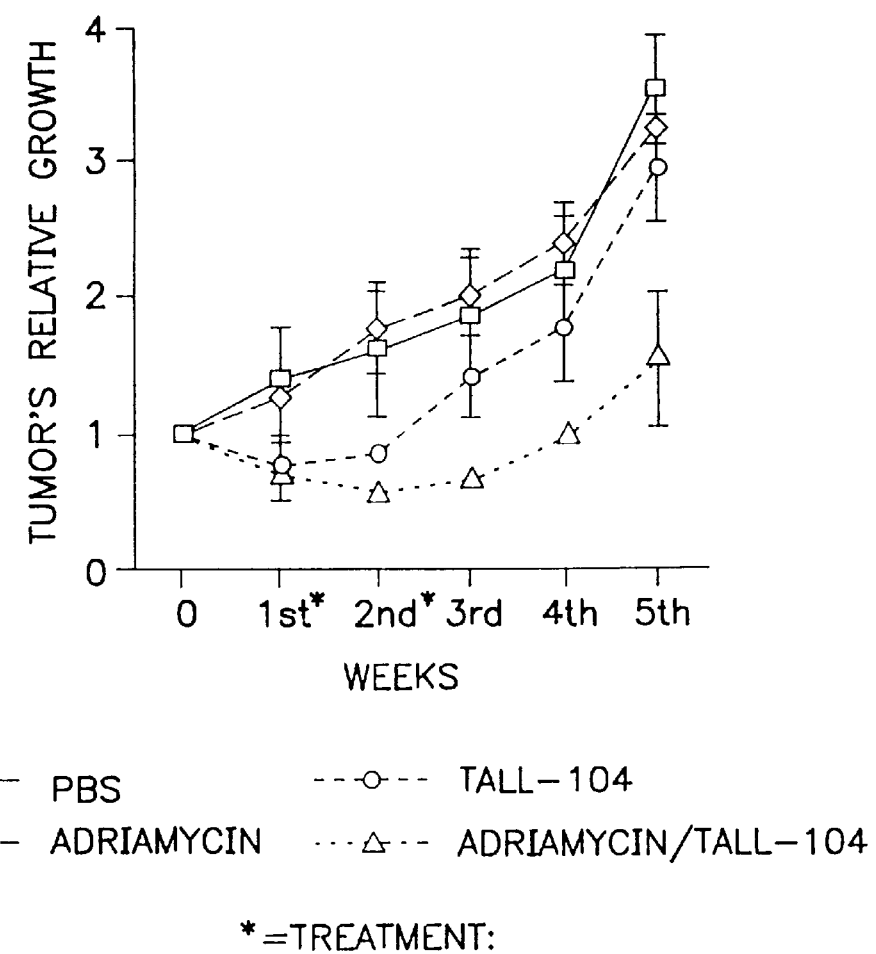
FIG. 2 is a growth curve of human MGC #1 tumor grafts in SCID mice receiving i.p. injections of PBS, adriamycin and/or TALL-104 cells.

The examples below demonstrate that the combination of chemotherapy (adriamycin) and adoptive immunotherapy with the MHC-unrestricted cytotoxic T cell line TALL-104 was effective in overcoming the total resistance to the single forms of treatment of a human gastric tumor-engrafted SCID mice (MGC #1). Although adriamycin and irradiated TALL-104 cells displayed strong cytostatic effects against these tumor cells in vitro, the in vivo experiments indicated that neither agent alone had significant antitumor effects in the SCID mouse model. The lack of in vivo activity might be merely due to the experimental conditions used, such as the time elapsed between tumor implantation and initiation of treatment, or the schedule and route of administration of adriamycin and TALL-104 cells. These conditions might have negatively affected the number of effector cells that migrated to, and persisted at, tumor site as well as the absorption of adriamycin, resulting in low seric levels of this drug. When chemotherapy and cell therapy were used in combination (at the same doses, schedule and route of administration), a dramatic antitumor effect against MGC #1 tumor grafts was observed: specifically, ⅓ of the animals had a lasting complete response (necrosis and fall out of the tumor masses) and ⅔ of them experienced a clinical response that, although partial and transient, was significant when compared with the total lack of antitumor effects displayed, in the same experiment, by the single treatments. Despite the relatively low number of mice used in the combined therapy experiment (n=6), these results are considered highly significant because spontaneous necrosis and regression of the subcutaneous tumors have never been observed and, on the other hand, a high reproducibility of tumor growth in a large number of implanted mice has been observed. Moreover, in the combined therapy group, the standard deviations of the average tumor volumes at the different time points were always very low (FIG. 2).

Several conclusions can be drawn from the antitumor effects of the chemo-immunotherapy protocol of the invention. Studies in immunocompetent mice bearing syngeneic tumors have shown that the combination of adoptively transferred T cells and some chemotherapeutic agents (in particular, cyclophosphamide) could successfully treat significant numbers of animals and tumor regression was primarily T-cell mediated [P. Greenberg et al, *J. Exp. Med.*, 161:1122–1134 (1985); M. Bookman et al, *J. Immunol.*, 139:3166–3170 (1987); and F. Fornelle et al, *Int. J. Cancer*, 42:952–957 (1988)]. In support of these data, other studies have shown that, in addition to direct tumor cytotoxicity, some chemotherapeutic drugs can modulate host immune responsiveness [M. Awwad et al, *Immunology*, 65:87–92 (1988) and R. North, *J. Exp. Med.*, 155:1063–1074 (1982)]. Because SCID mice, used as murine model in this study, are virtually devoid of functional T and B cells [G. Bosma et al, *Nature*, 301:527 (1983)], the antitumoral effects observed during and after chemo-immunotherapy are independent from the host's immune response and, therefore, different from the ones reported above [P. Greenberg et al, *J. Exp. Med.*, 161:1122–1134 (1985); M. Bookman et al, *J. Immunol.*, 139:3166–3170 (1987); and F. Fornelle et al, *Int. J. Cancer*, 42:952–957 (1988)]. In this respect, the use in this study of an immunocompromised animal to explore the antitumor effects of adriamycin-TALL-104 cell therapy excludes the role played by the host immune system in response to the combined chemo-immunotherapeutic approach. On the other hand, given that the majority of human neoplasms are non-immunogenic and, therefore, incapable of eliciting a significant T cell response in the autochthonous host, the SCID mouse model bearing a human tumor represents a very useful and relevant experimental system for testing the direct tumoricidal action of new therapeutic modalities.

In vitro experiments indicated an additive antiproliferative effect of low doses of adriamycin and TALL-104 cells against MGC #1 tumor cells. This finding is believed to translate in improved antitumor effects in an in vivo scenario in which sub-optimal concentrations of effector cells and/or drugs are likely to be present at tumor's site at different times during the treatment. In this regard, trafficking experiments using $^{51}$Cr-labeled, irradiated TALL-104 cells in SCID mice bearing MGC #1 tumors indicated that only few of the i.p. transferred effectors accumulated in tumor tissues (~4% of the total number of administered cells per gram of tumor tissue). Because effector cell infiltration within the tumor mass is a key feature for successful adoptive therapy, the synergistic antitumor effects of adriamycin and TALL-104 cells might, at least in part, be the consequence of an increased TALL-104 cell accumulation at tumor site. This hypothesis is supported by the results of Kawata et al, *Mol. Biother.*, 2:221–227 (1990), showing a two-fold accumulation of LAK cells into murine tumors after adriamycin injection, possibly consequent to a drug-induced increase in tumor vascularization which, in turn, would favor lymphocytic infiltration. The possibility, suggested in other systems [J. Gold et al, *J. Surg. Oncol.*, 58:212–221 (1995)], that adriamycin (administered before the cytotoxic cells) induced surface changes on the tumor thereby increasing its sensitivity to TALL-104 cell lysis, appears unlikely because in vitro pre-treatment of MGC #1 tumor cells with different doses of adriamycin did not have such an effect (not shown).

These examples illustrate the preferred methods of the invention. More particularly, the following examples demonstrate experiments which tested the combined effects of chemotherapy (adriamycin) with TALL-104 cells in SCID mice engrafted with a human tumor sample which is totally resistant to the single forms of treatment. These examples are illustrative only and do not limit the scope of the invention.

EXAMPLE 1

Preparation of Cells

The TALL-104 cell line was maintained at 37° C. in a humidified 10% $CO_2$ incubator in IMDM (Gibco-BRL, Grand Island, N.Y.) supplemented with 10% FBS (Sigma Chemical Co., St. Louis, Mo.) and 100 U/ml of recombinant human (rh) IL-2 (Chiron, Emeryville, Calif.). The cell line was repeatedly monitored for mycoplasma contamination using a commercial PCR kit (ATCC, Rockville, Md.). TALL-104 cells were γ-irradiated (4000 rads) prior to use in vitro and in adoptive therapy.

EXAMPLE 2

Implantation of Tumor

Frozen tumor fragments were minced through metal grids and centrifuged on AccuPrep™ lymphocyte gradients (Accurate Chemical, Westbury, N.J.) to remove dead cells and erythrocytes. The gastric tumor cells recovered at the interface were resuspended in complete medium and incubated at 37° C. in a humidified atmosphere at 5% $CO_2$.

Five- to 6-week-old CB-17 SCID mice (Charles River Laboratories, Wilmington, Mass.) were housed in a pathogen-free environment in The Wistar Institute Animal Facility. Mice were engrafted subcutaneously (s.c.) with metastatic pleural effusions (0.3×0.3 cm fragments) derived from a patient with gastric carcinoma (MGC #1).

Upon implantation, the biopsy sample grew as a local tumor mass that was subsequently harvested, cut, and serially passaged in other SCID mice. A portion of the tumors was frozen in IMDM containing 40% FBS and 10% DMSO (Sigma). Despite the highly metastatic behavior of this tumor in the original patient, the engrafted tumor fragments did not display metastatic properties in the mouse.

EXAMPLE 3

In Vitro Susceptibility of MGC #1 Cells to the Cytotoxic/Cytostatic Effects of TALL-104 Cells and Adriamycin A. Cytotoxicity Assays Irradiated TALL-104 cells were incubated at four different concentrations with a fixed number ($10^4$/well) of $^{51}$Cr-labeled MGC #1 cells for 18 hours. Percent specific $^{51}$Cr release was calculated from the mean of three replicates [A. Cesano et al, *Cancer Res.*, 56:3021 (1996)].

B. Cytokine Production

Irradiated TALL-104 cells ($2\times10^6$/ml) were incubated overnight at 37° C. with MGC #1 cells at an E:T ratio of 10:1. Cell-free conditioned medium was harvested, filtered and tested for the presence of IFN-γ, TNF-α, TNF-β, and GM-CSF using commercial ELISA kits (Endogen, R&D, Boston, Mass.) as described [A. Cesano et al, *Cancer Res.*, 56:3021 (1996)]. MGC #1 cell cultures incubated alone for 10 days were also tested for cytokine production.

C. Proliferation Assays

The cytostatic effects of irradiated TALL-104 cells (at four different concentrations) on MGC #1 cells ($10^4$/well) were tested in 18-h $^3$HTdR incorporation assays, as described [A. Cesano et al, *Cancer Res.*, 56:4444–4452 (1996)]. In experiments measuring the effects of adriamycin (Pharmacia, Piscataway, N.J.), MGC #1 cells ($10^4$/well) were cultured for 48 hours in the presence and absence of this drug at concentrations from 0.01 to 100 µg/ml before being pulsed with $^3$H-TdR.

D. Results

Figure 1B:
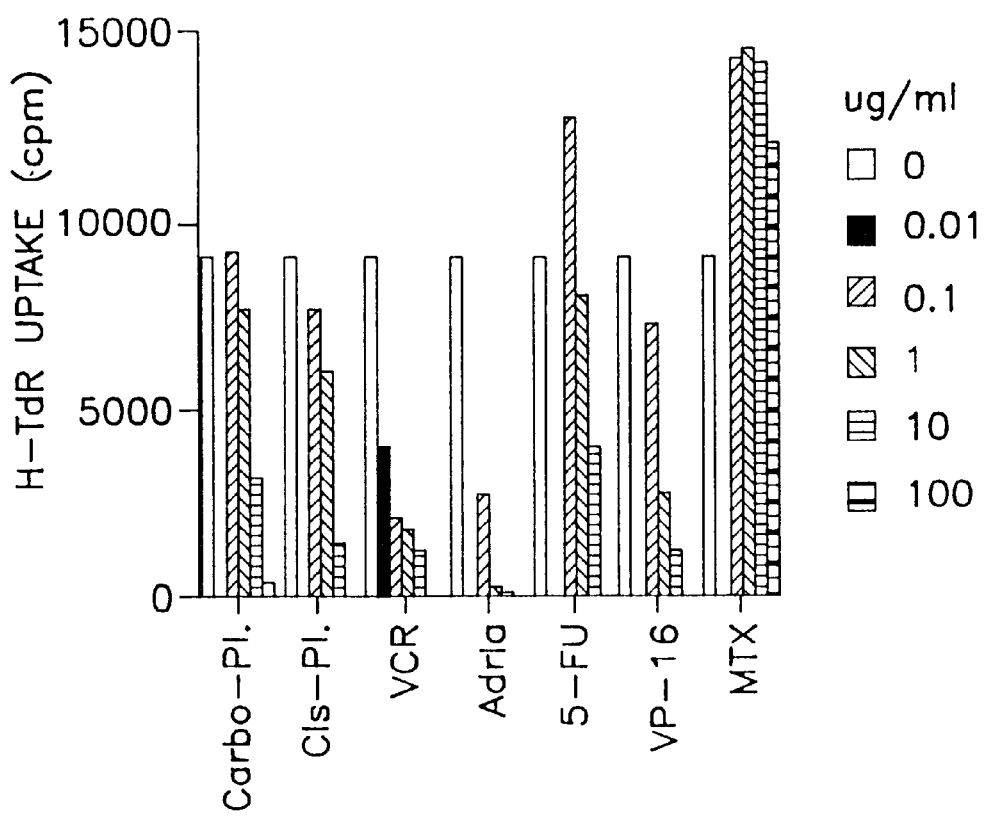
FIG. 1B illustrates effects of different chemotherapeutic drugs (at various doses) on the in vitro growth of MGC #1 tumor cells. Results of one representative experiment out of three performed are shown.

Gastric cancer cells recovered from the patient's biopsy specimen were totally resistant to lysis by irradiated TALL-104 cells, as measured in an 18-hour $^{51}$Cr-release assay, but were highly sensitive to their cytostatic activity (FIG. 1A). Incubation of irradiated TALL-104 cells with MGC #1 cells also resulted in the production of significant levels of IFN-γ, TNF-α, TNF-β, and GM-CSF (not shown). Among all the chemotherapeutic drugs tested for anti-proliferative activity against MGC #1 cells in vitro, adriamycin was the most potent, being able to inhibit proliferation of the tumor cells by 75% and 100% at the doses of 0.1 and 1 μg/ml, respectively (FIG. 1B).

EXAMPLE 4

Effect of Chemotherapeutic Drugs on TALL-104 Cell Functions

The effect of a variety of chemotherapeutic agents on TALL-104 cells was studied. Cytotoxicity, lymphokine production, and proliferation were assayed as described in Example 3 above using 0.01 to 100 μg/mL of the drugs listed in Table 1 below.

As can be seen from results provided in Table 1 below, dacarbazin (a nonclassic alkylating agent) did not affect cytotoxicity or lymphokine production. Adriamycin (an antibiotic), steroids (hormones), and cisplatin (an alkylating agent) had no affect on cytotoxicity and only marginally affected lymphokine production at therapeutic levels.

injected) and experimental mice were sacrificed. No significant difference in weight between the tumors of the treated mice and that of the control mice was detected (Table 2).

In the second set of experiments, mice bearing MGC #1 grafts were injected intralesionally with irradiated TALL-104 cells (or PBS) on alternate days for a total of 6 injections. All mice were sacrificed 1 month after the last injection and the tumor masses removed and weighed. Also in this setting, no significant difference in weight between the tumors of the treated mice and that of the controls was detected (Table 2).

The antitumor efficacy of TALL-104 cells was then evaluated after surgical removal of the primary tumors to create a clinical setting similar to that of minimal residual disease in cancer patients. Mice bearing 3-week-old MGC #1 grafts, which appeared highly mobile and non-adherent to the skin nor to the abdominal wall, underwent surgical excision of the tumor followed by TALL-104 cell therapy (or PBS injections), according to the protocol used in the first experiment. At surgery, the tumors weighed 0.781±0.112 g. One month after the last cell injection, all mice were sacrificed and necropsied. As shown in Table 2, TALL-104 cell treat-

TABLE 1

| Drug | Cytotoxicity | Lymphokine Production | Proliferation |
|---|---|---|---|
| Steroids | none | only marginally affected at therapeutic levels | decrease (dose dependent) |
| Carboplatin | decrease (at >100 μg/ml) | only marginally affected at therapeutic levels | decrease (dose dependent) |
| Adriamycin | none | only marginally affected at therapeutic levels | decrease (dose dependent) |
| Cisplatin | none | only marginally affected at therapeutic levels | decrease (dose dependent) |
| Dacarbazin | none | none | decrease (dose dependent) |
| Vincristine | decrease (dose dependent) | decrease (dose dependent) | decrease (dose dependent) |
| methotrexate | none | decrease (dose dependent) | decrease (dose dependent) |
| 5-FU | none | decrease (dose dependent) | decrease at >100 μg/mL |
| Cytoxan (as 4-Hc) | decrease (dose dependent) | decrease (dose dependent) | decrease (dose dependent) |
| Azathioprine | none | none | decrease at >100 μg/ml |

EXAMPLE 5

Antitumor Effects of TALL-104 Cells in SCID Mice

A. Treatment Protocols

All treatments were initiated 3 weeks after implantation of the tumor fragments (except when specified otherwise), when a significant macroscopic growth of the tumors was appreciable. Each treatment group consisted of 4–6 mice. In the first experiment, γ-irradiated TALL-104 cells ($2 \times 10^7$/mouse in 500 μl PBS) or PBS alone were administered i.p. daily for 2 weeks; in a second experiment, $10^7$ cells/mouse in 100 μl PBS or PBS alone were injected intralesionally on alternate days, for a total of six injections. In a third experiment, mice underwent surgical removal of the primary tumor mass followed by i.p. injection of either irradiated TALL-104 cells ($2 \times 10^7$/mouse) or PBS alone, daily for 2 weeks.

Differences between treatment groups were tested for significance by the Student's t-test for unpaired data. P<0.05 was considered significant.

B. Results

In the first set of experiments, irradiated TALL-104 cells were injected i.p. every day for 2 weeks in SCID mice engrafted 3 weeks earlier with MGC #1 tumor fragments. Four weeks after completion of therapy, all controls (PBS ment did not have a significant inhibitory effect on the local regrowth of the tumor cells in the mice; these in vivo data are in contrast with the observed anti-proliferative effects displayed by TALL-104 cells against MGC #1 cells in vitro (FIG. 1A).

TABLE 2

Effects of Single Treatment with Either TALL-104 Cells or Adriamycin on the Local Growth of MGC #1 Tumor Grafts

| Experiment | No. of Mice | Treatment[a] (2 wks duration) | Route and Schedule of administration | Tumor weight[b] (SD)[c] |
|---|---|---|---|---|
| 1 | 6 | PBS | i.p.[d] daily | 0.957 (0.208)[b] |
| 1 | 6 | TALL-104 | i.p. daily | 0.888 (0.606) |
| 2 | 6 | PBS | i.t. alternate days | 1.227 (0.137) |
| 2 | 6 | TALL-104 | i.t. alternate days | 1.298 (0.372) |
| 3 | 4 | surgery + PBS | i.p. daily | 0.752 (0.166) |
| 3 | 4 | surgery + TALL-104 | i.p. daily | 0.748 (0.279) |

TABLE 2-continued

Effects of Single Treatment with Either TALL-104 Cells or Adriamycin on the Local Growth of MGC #1 Tumor Grafts

| Experiment | No. of Mice | Treatment[a] (2 wks duration) | Route and Schedule of administration | Tumor weight[b] (SD)[c] |
|---|---|---|---|---|
| 4 | 6 | PBS | i.p. weekly | 0.99 (0.165) |
| 4 | 6 | Adriamycin | i.p. weekly | 1.119 (0.234) |

[a]TALL-104 cells were γ-irradiated (40 Gy) prior each injection.
[b]Grams.
[c]Standard deviation.
[d]intraperitoneal; i.t. = intratumoral.

EXAMPLE 6

Chemotherapy

Based on the in vitro observation that MGC #1 tumor cells were highly sensitive to the cytotoxic effects of adriamycin (FIG. 1B), this drug was chosen for the in vivo study. Two groups of mice bearing MGC #1 tumor grafts (n=6) were treated with two i.p. injections of adriamycin (30 mg/m$^2$ at 1 week interval) or PBS. Autopsy performed 1 month after the last injection failed to reveal significant differences in tumor weights between controls and adriamycin-treated mice (Table 2).

EXAMPLE 7

Chemo-immunotherapy

Figure 3A:
FIG. 3A is the macroscopic appearance of the MGC #1 tumor mass grown in a mouse that received adriamycin/TALL-104 cell combined treatment before therapy.
Figure 3B:
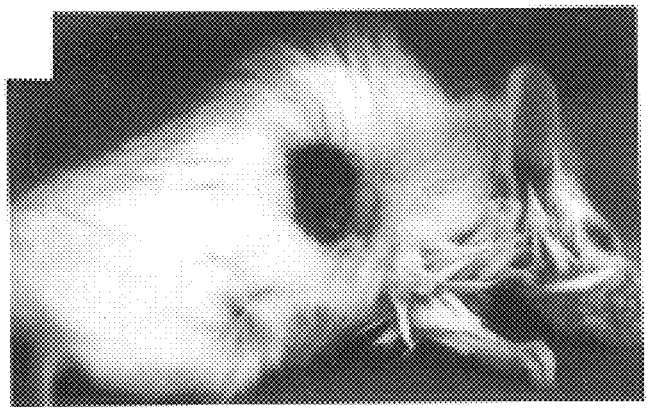
FIG. 3B is the macroscopic appearance of the mouse of FIG. 3A showing the scar tissue remaining as a consequence of a 2-week therapy when the tumor mass became necrotic and fell out.

In the attempt to overcome the high resistance shown by MGC #1 tumor grafts to treatment with either chemotherapy or adoptive therapy, a combined regimen based on sequential administration of two cycles of adriamycin followed by TALL-104 cells was tested for therapeutic efficacy in SCID mice (n=6) bearing MGC #1 tumor grafts. In the last experiment, mice received two i.p. doses of adriamycin (day 1 and 7) and irradiated TALL-104 cells (2×10$^7$/mouse) from day 2 to 6 and from day 8 to 14. Control groups (n=4) received PBS, adriamycin or TALL-104 cells alone. Tumor masses were measured (using a millimeter vernier caliper) before therapy and then, at weekly intervals, for the entire 5 week follow-up period. Results of this experiment are summarized in FIG. 2. After the first week of treatments, no statistically significant differences were found between the average tumor sizes in the different groups of mice. Noteworthy, however, two mice that had received combined therapy presented a macroscopically noticeable tumor necrosis at the end of the first week of treatment; necrosis progressed until the tumor mass fell out in both mice, leaving behind a necrotic scar during the second week of follow-up (FIG. 3). For this reason, the values relative to tumor measurement in these two mice do not show in FIG. 2 and could not be included in any statistical calculation made after the second follow-up week. At the end of the second week of treatment, the tumors of the four remaining adriamycin/TALL-104 cell-treated animals were significantly smaller as compared to those present on PBS- or adriamycin-treated mice (p<0.05 and p<0.002, respectively). By contrast, no statistically significant difference was observed, at this time point, between adriamycin/TALL-104 cell-treated mice and the group of mice that had received TALL-104 cells alone. In fact, in both groups, a discrete shrinkage (36% and 20%, respectively) in tumor size was noted. Tumor reduction was already detectable (but not statistically significant) at the end of week 1. Starting from the end of week 3 (1 week after all treatments had been halted), while the tumors shrinkage stabilized in the group of mice that had received the combined therapy (~36%), tumor growth progressed in all other groups of mice, including the one that received TALL-104 cells alone. As a result, the difference in tumor volume between adriamycin/TALL-104 cell-treated animals and the ones receiving either PBS, adriamycin or TALL-104 cells alone was statistically significant (p<0.02, p<0.001 and p<0.05 respectively). Similar results were observed at the end of the fourth week. By the end of the fifth week, the tumor volume in the mice treated with TALL-104 cells alone increased to the point that it became very close to the one seen in PBS or adriamycin-treated mice. These data showed that, although TALL-104 cells by themselves did have antitumor activity against MGC #1 tumor growth during the first 2 weeks of treatment, these effects were transient and the tumors quickly progressed as soon as the cell injections were halted. The three control groups were sacrificed at the end of week 5 because of high tumor burden (around 3 times the volume of the tumor seen in mice treated with the combined regimen). Mice treated with adriamycin/TALL-104 cells were followed up for 4 more weeks: during this time the tumors slowly but progressively grew reaching, at the end of week 9, the size of the tumors displayed by the group of mice treated with TALL-104 cells alone at week 5 (not shown). The experiment was ended at this point.

Numerous modifications and variations of the present invention are included in the above-identified specification and are expected to be obvious to one of skill in the art. Such modifications and alterations to the compositions and processes of the present invention are believed to be encompassed in the scope of the claims appended hereto.

What is claimed is:

1. A method of treating cancer in a mammal comprising the steps of
administering to the mammal a course of therapy with an effective amount of a chemotherapeutic agent selected from the group consisting of adriamycin and cisplatin; and
administering a course of therapy with an effective amount of TALL-104 cells ATCC Accession No. CRL11386, which cells have been modified by stimulation in vitro by treatment with a cytokine and gamma irradiation at a dose suitable to irreversibly arrest cell proliferation but not interfere with the cytotoxic activity of the cells, said modified cells characterized by irreversibly arrested cell proliferation and non-MHC restricted cytotoxic activity said TALL-104 administering step occurring during or after said administration of said chemotherapeutic agent.

2. The method according to claim 1, wherein the cell therapy is administered during the course of treatment with the chemotherapeutic agent.

3. The method according to claim 1, wherein the cell therapy is administered after the course of treatment with the chemotherapeutic agent.

4. The method according to claim 1, wherein the chemotherapeutic agent is adriamycin.

5. The method according to claim 1, wherein the cells have been modified by stimulation in vitro by treatment with IL-2 to enhance the cytotoxic activity of the TALL-104 cells and gamma-irradiation at a dose suitable to irreversibly arrest cell proliferation but not interfere with the cytotoxic activity of the cells.

6. The method according to claim 1, wherein the chemotherapeutic agent is cisplatin.

7. The method according to claim 1 wherein said mammal has a drug-resistant tumor.

8. The method according to claim 1 wherein said administration of said chemotherapy and cell therapy has an anti-cancer effect which exceeds the additive anti-cancer effects of said chemotherapy and said cell therapy.

9. The method according to claim 1 wherein said administration of said chemotherapy and cell therapy has an anti-cancer effect which exceeds the anti-cancer effects of either chemotherapy or cell therapy.

* * * * *